United States Patent [19]

Schmitt et al.

[11] Patent Number: 4,830,009

[45] Date of Patent: May 16, 1989

[54] METHOD FOR ELECTRICAL STIMULATION, MORE PARTICULARLY FOR THE TREATMENT OF SCOLIOSIS

[75] Inventors: Otmar Schmitt, Neunkairchien; Heinz Mittelmeier, Homburg, both of Fed. Rep. of Germany

[73] Assignee: Oscobal AG, Selzach, Switzerland

[21] Appl. No.: 844,351

[22] Filed: Mar. 26, 1986

[30] Foreign Application Priority Data

Apr. 1, 1985 [EP] European Pat. Off. ........... 85810144

[51] Int. Cl.$^4$ .............................................. A61N 1/36
[52] U.S. Cl. .................................................. 128/421
[58] Field of Search ........ 128/419 PG, 420 A, 420 R, 128/421, 422

[56] References Cited

U.S. PATENT DOCUMENTS

| | | | |
|---|---|---|---|
| 2,808,826 | 10/1957 | Reiner et al. | 128/422 |
| 3,983,881 | 10/1976 | Wickham | 128/421 |
| 4,026,301 | 5/1977 | Friedman et al. | 128/421 |
| 4,233,986 | 11/1980 | Tannenbaum | 128/422 |
| 4,326,534 | 4/1982 | Axelgaard et al. | 128/421 |
| 4,533,548 | 12/1985 | Varrichio et al. | 128/421 |
| 4,574,807 | 3/1986 | Hewson et al. | 128/419 PG |
| 4,580,570 | 4/1986 | Sarrell et al. | 128/421 |

Primary Examiner—William E. Kamm
Assistant Examiner—David Shay
Attorney, Agent, or Firm—Pravel, Gambrell, Hewitt, Kimball & Krieger

[57] ABSTRACT

The apparatus for electrical stimulation is more particularly adapted for the treatment of scoliosis and comprises an electrical circuit which delivers individual pulses having a duration of about 1 ms, an amplitude of about 150 V, a constant current intensity of about 75 mA and a frequency of 100 Hz as well as series of pulses with rising amplitude and a ramp up phase of about 2 s, followed by holding phase of about 2 s and a time off between two series of pulses of about 10 s. The apparatus further comprises three channels, whereby the first channel is applied on the side of the curvature, the second channel on the side of the counter curvature and the third channel on the abdominal musculature, whereby all channels are fed simultaneously.

1 Claim, 2 Drawing Sheets

METHOD FOR ELECTRICAL STIMULATION, MORE PARTICULARLY FOR THE TREATMENT OF SCOLIOSIS

BACKGROUND OF THE INVENTION

The present invention relates to an apparatus for electrical stimulation, more particularly for the treatment of scoliosis with at least one channel for a pair of electrodes and an electrical circuit for adjusting the duration, amplitude and frequency of individual pulses as well as the time off between the individual pulses and the evolution in time of series of pulses, whereby the amplitude of the individual square pulses increases in an initial phase, then reaches a hold level and finally decreases again. Such an apparatus is known from the U.S. Pat. No. 4,326,534. Moreover, other embodiments of this apparatus are described in the two successive U.S. Pat. Nos. 4,342,317 and 4,408,609 of the same inventor.

Particularly in case of scoliosis, for which the above mentioned apparatus according to the invention is specifically provided, that is in case of spinal deformities which are characterized by lateral curvature and torsion of the spine, there is pathologic displacement of the pattern of muscular fibres which necessitates a particular respond by electrical stimulation for achieving a curvature correction. Recent researches have shown that in case of scoliosis the normal pattern of repartition of the muscular fibres with about 64% of tonus fibres and 36% of contraction fibres is displaced in favour of the tonus fibres. These tonus fibres, which have the task to maintain a certain condition of continuous tension in the musculature, are less influenced by the electrophysiological stimulation because their membrane-properties are modified. In this way, the patients have less contraction fibres at disposal, these fibres exhibiting a good reaction to electrophysiological stimulation excitations, thus being of decisive importance for the extent of the muscular effect on the curvature of the spine. Recent experiments on animals have shown that it is possible by high frequency stimulation to change backwards the number of the tonus fibres, thus permitting correction of the disturbed balance in favour of the tonus fibres.

Principally, such a therapy should guarantee, like other ones, an optimal success in the shortest period of treatment. If however too high intensities of current are utilized which are of significance for the degree of muscle stimulation and consequently for the success of the treatment, skin pains appear although in various manner in dependence on different parameters of the current. On the other hand, inflammatory skin excitations at the electrodes appear in case of a long period of application. It is therefore necessary to provide optimal pulses of current during a relative short period of treatment.

The apparatus described in the three above mentioned Patents is utilized, after a short period of acclimatization, for the simulation during the hours of sleep. However, it is now recognized that this is insufficient because, in order not to disturb the sleep, one works only with relative low current intensities, greater current intensities producing such strong muscle contractions that the patient awakens. Further, the long period of application of the electrodes leads to the already mentioned skin excitations. Moreover, the mentioned apparatus produces increasing and decreasing series of pulses which begin with a very short pulse duration of 10 μs, then become longer with increasing duration of the series of pulses and amplitude and reach the greatest pulse duration of 200 μs during the hold level. From the physiological point of view of the membrane, this is an unfavourable form of a series of pulses because of the very short duration of the initial pulses. Because the pulses are applied only in the domain of the lateral intercostal musculature, they are obviously not sufficient for causing the corresponding effect in the domain of the extremely important paravertebral musculature, that is immediately beside the spine and they are more particularly not able to cause also here the essential indirect excitation on the intercostal nerves. As a consequence, it was necessary to work with 2-channel stimulators as mentioned in the two indicated, successive Patents, the stimulators working either with overlapping or alternating series of pulses. In this case, two channels are each time necessary for reaching the different muscular groups of a curvature. This presents however the disadvantage that the second channel is no longer at disposal for the counter curvature of the mostly S-shaped scoliosises. This means that the muscle excitation is limited to only a part of the scoliosis. Moreover, the short pulses have the effect that only muscle fibre lying in the surface of the muscle groups are attained, these fibres having the lowest excitation threshold, and not the central zones with a high excitation threshold.

Moreover, the said apparatuses and also other known apparatuses, i.e. according to U.S. Pat. Nos. 4,102,348 and 4,539,993 work in accordance with the low frequency concept, that is with pulse repetition frequencies of about 30 Hz in order not to create a fatigue of the muscle. However, it is known that a muscle which is not fatigued during training is not sufficiently trained. It is essential in this respect that recuperation pauses be provided. It has been found that the low frequency pulses feed the tonus fibres of the musculature which, although being capable of continuous working do not possess the cability of a rapid force development which would be necessary for acting on the scoliosis deformities in order to correct them.

SUMMARY OF THE INVENTION

It is therefore an object of the present invention to provide an apparatus for electrical stimulation capable of causing a better strengthening of the muscle within a substantially shorter period of treatment. To solve this problem, the electrical circuit delivers individual pulses of 0.5–5 ms duration, an amplitude of 100–200 V, a constant current of 50–100 mA intensity and a frequency of 75–125 Hz as well as series of pulses with a ramp up period 2 s and a hold period of 1–2 s, whereby the time offs between two series of pulses are of 8–12 s.

BRIEF DESCRIPTION OF THE DRAWINGS

The invention will be described further by way of example with reference to the accompanying drawings in which.

DESCRIPTION OF THE PREFERRED EMBODIMENT AND METHOD

Figure 1:
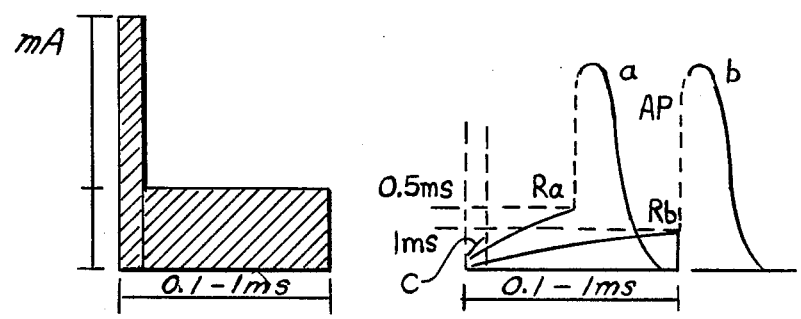
FIG. 1 shows the equivalent diagram of the pulse deformation from different tissue resistances.

Detailed researches have shown that pulses applied from the outside on the skin are distorted and more particularly also diminished by the different parts of the tissue. It is possible to represent the different portions of the tissue by an equivalent circuit comprising ohmic resistances connected in series and capacitive resistances (capacitors with finite insulation, that is with losses) connected in prallel which cause a reduction of the initial value of the amplitude and a decrease of the slope of the ramp up portion of the pulses. This effect exists more particularly in the deep regions of the tissue.

The square pulse with a vertical rising edge (see FIG. 1 or 2) is an ideal pulse shape for releasing a conducted excitation at excitable membranes. The quicker is produced the depolarization, the faster is overcome a determined excitation threshold. Any delay in the depolarization has for consequence a diminution of the excitability, that is an increase of the excitation threshold. This remains true also for the period of action of the depolarization. The longer a depolarizing current flows, the smaller is the excitation threshold, the shorter acts a depolarizing current, the higher is the excitation threshold. This may be illustrated by means of the schematic pulse deformations according to FIG. 1. The square pulse is the pulse shape which causes the greatest rising slope also in the deep located regions of the tissue. The individual pulse of sufficient duration of about one ms implies the smallest excitation threshold Rb for releasing a conducted excitation, see curve b. A shorter pulse, i.e. shorter than 0.5 ms gives rise to a higher excitation threshold Ra so that a stronger individual pulse must be applied from the outside in order to cause a conducted excitation, see curve a.

Already predistorted individual pulses like the ones which are utilized without exception in the known apparatuses are further distorted by the ohmic and capacitive resistances of the tissue so that in the deep regions of the tissue in which an excitation is prioritary necessary—deep muscle layers of th paravertebral musculature, resp. intercostal nerves—no sufficient rising slope, resp. current amplitude and hold level are at disposal for releasing a conducted excitation, see curve c. It is mentioned in the literature, resp. in the above mentioned american Patents that square pulses would be desirable but that a certain deformation of these pulses must be taken into consideration. The researches which have confirmed the equivalent diagram and the pulse deformation shapes have shown however that it is of importance to produce pulses with a rigorous and possibly of ideal square shape. In order to release an excitatin it is further necessary to provide a minimum current amplitude (Rheobase), because below this amplitude, a depolarizing pulse has no effect. For the small current intensities which must be applied, relative long pulses of one ms duration are necessary, like for the muscle, resp. motor conduction of nervous membranes. In order to have a sufficient reserve of security in the deep regions of the tissue, it is necessary to work with a current of at least 50 mA and a pulse duration of at least 0.5 ms. The intensity depends on the value of the resistances of the tissue which are determined during the examination.

From these knowledges and considering the mentioned object of the invention which is to attain an optimal success within a shortest period of treatment, that is first of all to make the tonus fibres to regress and to restore the disturbed balance in favour of the contraction fibres and to realize a so-called maximal training, because a substantially greater training effect is achieved when training for only a short time with maximal muscle tension than when training continuously over a long period of time with a small muscle tension, it is an aim of providing an apparatus capable of delivering the following parameters of current:

1. Square pulses with steepest possible rising edges, with a pulse duration of 0.5–5 ms, preferably 1 ms,
2. an amplitude of the individual pulses of 100–200 V, preferably 150 V which, for a corresponding resistance of the tissue and adjustment corresponds to a current intensity of at least 50 mA to maximum 100 mA, in order to reach a maximum penetration depth,
3. a pulse frequency of 75–125 HZ, preferably 100 Hz for normalization of the composition of the types of fibres,
4. a series of pulses of at least 2 to preferably and maximally 4 s with a rising phase of the amplitude of the pulses of about 2 s duration and a hold phase of 1–2 s duration (see FIG. 3),
5. three channels synchronized together the amplitude of which being capable to be individually adjusted, and
6. means for maintaining constant the adjusted current intensity, in order to avoid a variation of the intensity of the current when the resistances vary.

Figure 3:
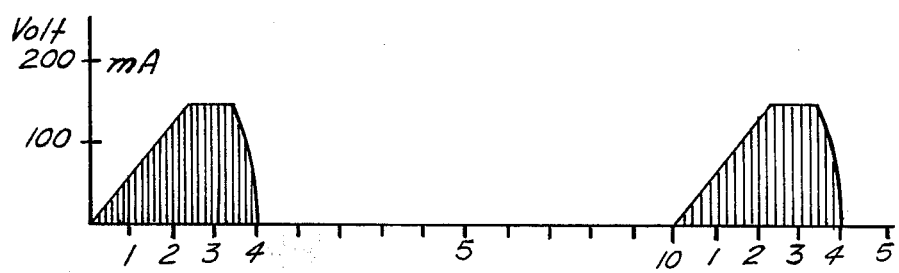
FIG. 3 shows a series of pulses of the apparatus according to the invention.
Figure 4:
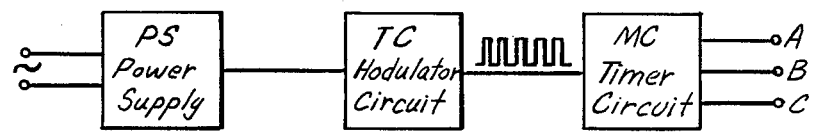
FIG. 4 shows the block diagram of the electrical circuit for the apparatus according to the invention.
Figure 5:
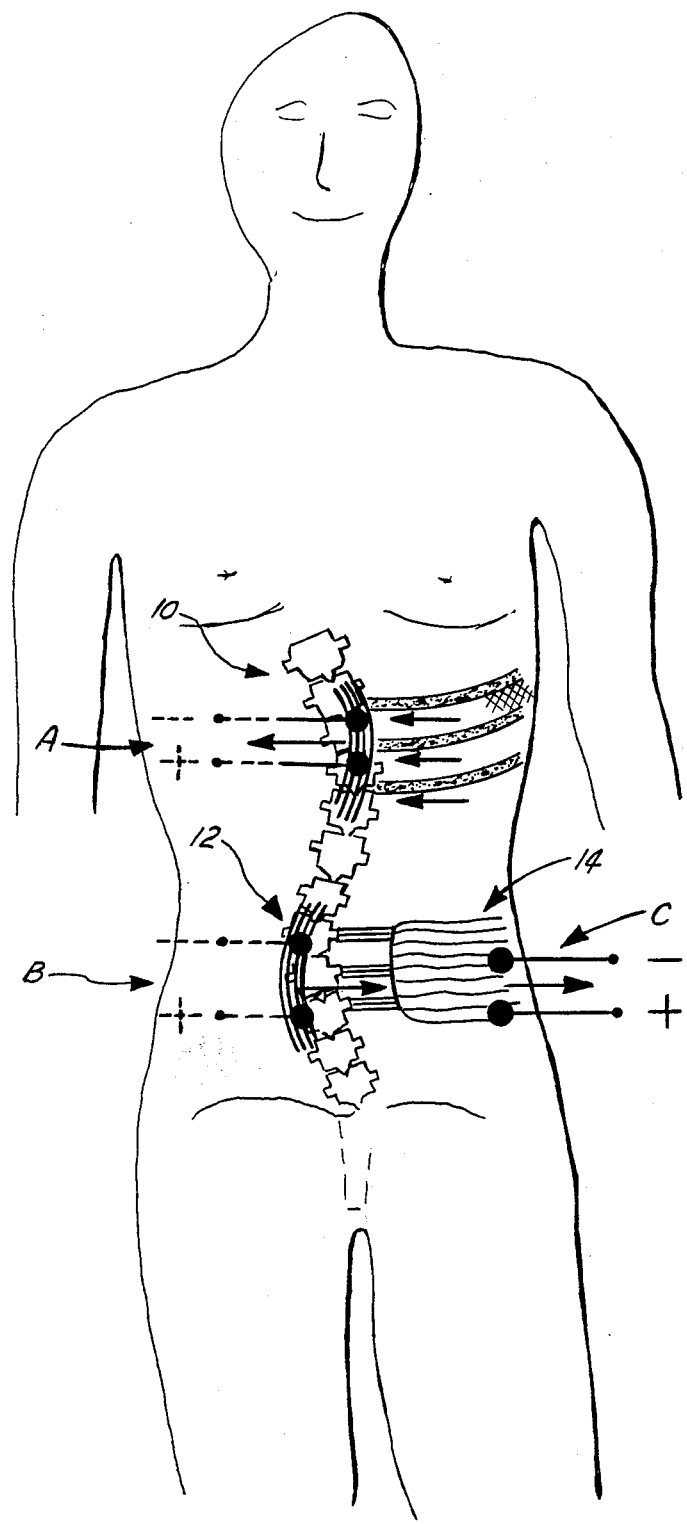
FIG. 5 shows a schematic illustration of the placement of portions of the apparatus according to the invention.

FIG. 4 shows a simplified block diagram of such an apparatus for electrical stimulation. The feeding part PS connected to the mains is provided for delivering a constant voltage of plus and minus 15 V as well as a voltage adjustable from 0 to 200 V and it contains a circuit for maintaining constant an intensity of the current which is adjustable between 50 and 100 mA. The feeding part is connected to a timing circuit TC in which square pulses of i.e. 1 ms and a frequency of 100 HZ are produced, whereby the amplitude of the square pulses is variable. It is clear that other pulses with other frequencies in the mentioned range may also be produced. The pulses are delivered to a modulator and current amplifier circuit MC in which they are transformed in series of pulses, whereby the amplitude rises i.e. within 2 s from 0 to 150 V then is maintained constant for 2 s and finally decreases toward 0, a time off of 10 s being provided before the next series of pulses as shown in FIG. 3. The intensity of the current is maintained at a constant value of i.e. 75 mA as already mentioned. The series of pulses may be delivered in synchronism on all three channels A, B and C. The particular pulse shape and its duration permits from a position of the electrodes to stimulate simultaneously all muscle groups of a curvature which are significant for the correction of the scoliosis. If the first electrode pair (channel) A is provided on the curvature 10, the second electrode pair on the counter current 12 which is present in most cases and the third electrode pair C on the inclined abdominal musculature 14, a very rapid and thorough healing is achieved.

Figure 2:
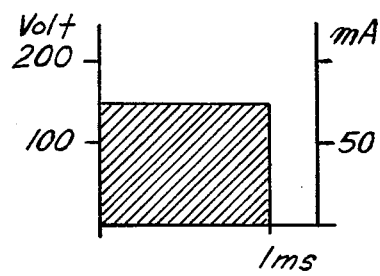
FIG. 2 shows a single pulse of the apparatus according to the invention.

For most apparatuses it is advantageous to determine in advance the duration of the series and the time offs and also to maintain constant the duration of the individual pulses and their frequency of repetition. However, for special applications, it should be advantageous to have the possibility of varying all parameters within determined limits and more particularly to vary certain parameters of the different channels independently from each other. It is more particularly important for such an apparatus to ensure that possibility ideal square shaped pulses, that is pulses with possibly steep rising edges are produced because as shown in FIG. 1 the pulses are strongly distorted in the skin. Treatments with such an apparatus, that is with a very good square shaped pulse of ms duration and a frequency of 100 HZ as well as series of pulses according to FIG. 3 with a hold level of 150 V and a constant current intensity of 75 mA permit to achieve treatment periods of 20–30 Min. per day to the contrary of periods of treatment of as much as 16 hours with known apparatuses. This permits to undertake the treatment during the day, i.e. after the school or in the evening before going to sleep and the night rest is not disturbed. Moreover, an excitation of the skin can be avoided because of the short period of application.

We claim:

1. A method of treating signal curvature deformities, in particular scoliosis of human patients, comprising the steps of:
    (a) applying a first electrode pair corresponding to the first channel (A) of an apparatus for delivering pulses, at a position on the side of the curvature so that muscle groups of the curvature that can correct the scoliosis can be stimulated by the first electrode pair at the curvature,
    (b) applying a second electrode pair corresponding to the second channel (B) of said apparatus, on the counter curvature,
    (c) applying a third electrode pair corresponding to a third channel (C) of the apparatus on the inclined abdominal musculature; and
    (d) applying synchronously to the three electrode pairs a series of pulses with a ramp up period of 2 s, a hold period of 1–2 s, and time offs between two series of pulses of 8–12 s, said pulse series being composed of individual square pulses with a vertical rising edge having a duration of 0.5–5 ms, an amplitude of 100–200 V, a constant current of 50–100 mA intensity and a frequency of 75–125 Hz.

* * * * *

UNITED STATES PATENT AND TRADEMARK OFFICE
CERTIFICATE OF CORRECTION

PATENT NO. : 4,830,009

DATED : MAY 16, 1989

INVENTOR(S) : SCHMITT et al.

It is certified that error appears in the above-identified patent and that said Letters Patent is hereby corrected as shown below:

In item [75] on title page, change "Neunkairchien" to --Neunkirchen--.

In claim 1, line 1, change "signal" to --spinal--.

Signed and Sealed this

Fifteenth Day of October, 1991

Attest:

HARRY F. MANBECK, JR.

*Attesting Officer*     *Commissioner of Patents and Trademarks*